(12) United States Patent
Agell et al.

(10) Patent No.: US 11,721,358 B2
(45) Date of Patent: Aug. 8, 2023

(54) SYSTEM AND METHOD FOR CALCULATING CARDIOVASCULAR HEARTBEAT INFORMATION FROM AN ELECTRONIC AUDIO SIGNAL

(71) Applicant: Stichting IMEC Nederland, Eindhoven (NL)

(72) Inventors: Carlos Agell, Eindhoven (NL); Evelien Hermeling, Soerendonk (NL); Vojkan Mihajlovic, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 543 days.

(21) Appl. No.: 16/903,895

(22) Filed: Jun. 17, 2020

(65) Prior Publication Data

US 2020/0395040 A1 Dec. 17, 2020

(30) Foreign Application Priority Data

Jun. 17, 2019 (EP) .................... 19180559

(51) Int. Cl.
*A61B 5/00* (2006.01)
*G10L 25/66* (2013.01)
(Continued)

(52) U.S. Cl.
CPC .............. *G10L 25/66* (2013.01); *A61B 5/024* (2013.01); *A61B 5/02405* (2013.01);
(Continued)

(58) Field of Classification Search
CPC ......... G10L 25/66; G10L 25/90; A61B 5/024; A61B 5/02405; A61B 5/7217;
(Continued)

(56) References Cited

U.S. PATENT DOCUMENTS 10,643,639 B2* 5/2020 Zadgaonkar ............ G10L 15/22
2007/0213981 A1* 9/2007 Meyerhoff .............. G10L 17/26
704/243
(Continued)

FOREIGN PATENT DOCUMENTS

WO 2018146690 A1 8/2018

OTHER PUBLICATIONS

Extended European Search Report and Written Opinion, EP Application No. 20180436.6, dated Oct. 19, 2020, 10 pages.
(Continued)

*Primary Examiner* — Rex R Holmes
(74) *Attorney, Agent, or Firm* — McDonnell Boehnen Hulbert & Berghoff LLP

(57) ABSTRACT

A device for calculating cardiovascular heartbeat information is configured to receive an electronic audio signal with information representative of a human voice signal in the time-domain, the human voice signal comprising a vowel audio sound of a certain duration and a fundamental frequency; generate a power spectral profile of a section of the electronic audio signal, and detect the fundamental frequency (F0) in the generated power spectral profile; filter the received audio signal within a band around at least the detected fundamental frequency (F0) and thereby generating a denoised audio signal; generate a time-domain intermediate signal that captures frequency, amplitude and/or phase of the denoised audio signal; detect and calculate heartbeat information within a human cardiac band in the intermediate signal.

20 Claims, 12 Drawing Sheets

(51) Int. Cl.
*A61B 5/024* (2006.01)
*A61B 7/04* (2006.01)

(52) U.S. Cl.
CPC .......... *A61B 5/7217* (2013.01); *A61B 5/7253* (2013.01); *A61B 7/04* (2013.01)

(58) Field of Classification Search
CPC ........... A61B 5/7253; A61B 7/04; A61B 5/02; A61B 8/02
See application file for complete search history.

(56) References Cited

U.S. PATENT DOCUMENTS

| | | | | |
|---|---|---|---|---|
| 2012/0265024 | A1* | 10/2012 | Shrivastav | ............. G16H 50/30 600/300 |
| 2014/0122063 | A1* | 5/2014 | Gomez Vilda | .......... G10L 19/02 704/200.1 |
| 2018/0153427 | A1 | 6/2018 | Al-Jumaily et al. | |

OTHER PUBLICATIONS

Barros, Allan Kardec, and Noboru Ohnishi. "Heart instantaneous frequency (HIF): an alternative approach to extract heart rate variability." IEEE transactions on biomedical engineering 48, No. 8 (2001): 850-855.

Kumar, D., P. Carvalho, M. Antunes, R. P. Paiva, and J. Henriques. "Noise detection during heart sound recording using periodicity signatures." Physiological measurement 32, No. 5 (2011): 599-618.

Yang, Chenxi, and Negar Tavassolian. "Pulse transit time measurement using seismocardiogram, and in-ear acoustic sensor." 2016 IEEE Biomedical Circuits and Systems Conference (BioCAS). pp. 188-191.

Scanlon, Michael V. "Acoustic sensors in the helmet detect voice and physiology." In Sensors, and Command, Control, Communications, and Intelligence (C3I) Technologies for Homeland Defense and Law Enforcement II, vol. 5071, pp. 41-51. International Society for Optics and Photonics, 2003.

Khandelwal, Saransh, Simrat Sahni, Sanjeev Kumar, and Amod Kumar. "Pressure Sensor Based Estimation of Pulse Transit Time." International Journal of Information & Computation Technology 4 (2014): 1321-1328.

Schuller, Björn, Felix Friedmann, and Florian Eyben. "Automatic recognition of physiological parameters in the human voice: Heart rate and skin conductance." In 2013 IEEE International Conference on Acoustics, Speech and Signal Processing, pp. 7219-7223. IEEE, 2013.

Mesleh, Abdelwadood, Dmitriy Skopin, Sergey Baglikov, and Anas Quteishat. "Heart rate extraction from vowel speech signals." Journal of computer science and technology 27, No. 6 (2012): 1243-1251.

* cited by examiner

SYSTEM AND METHOD FOR CALCULATING CARDIOVASCULAR HEARTBEAT INFORMATION FROM AN ELECTRONIC AUDIO SIGNAL

CROSS-REFERENCE TO RELATED APPLICATIONS

The present application is a non-provisional patent application claiming priority to European Patent Application No. EP 19180559.7, filed Jun. 17, 2019, the contents of which are hereby incorporated by reference.

FIELD OF THE DISCLOSURE

The present description relates generally to electronic systems for calculating cardiovascular heartbeat information and more specifically to an electronic system for calculating cardiovascular heartbeat information from an electronic audio signal input.

BACKGROUND

There is an increasing need for providing cardiovascular heartbeat and heartrate information from human subjects. Some techniques provide such information using non-contact sensing techniques. An example method is shown in "*Heart Rate Extraction from Vowel Speech Signals*", by A. Mesleh et al, Journal of Computer Science and Technology 27(6): 1243-1251, November 2012. Another known technique is described in "*Automatic Recognition of Physiological Parameters in the Human Voice: Heart Rate and Skin Conductance*", by B. Schuller et al, Proceedings of IEEE International Conference on Acoustics Speech and Signal Processing, pp. 7219-7223, 2013.

There is a motivation to improve current state of the art electronic systems and methods for non-contact extraction of heart rate information from electronic human voice audio signals.

SUMMARY

A system and method for calculating cardiovascular heartbeat information is described herein, which allows calculating a subject's cardiovascular heartbeat information from an electronic audio signal recorded from the subject. According to an example embodiment, the electronic system is able to calculate the subject's cardiovascular heartbeat information from an electronic audio signal using calculations in the time domain. According to an example embodiment, the electronic system provides cardiovascular heartbeat information in a beat by beat basis, thereby being able to provide heart rate (HR), heart rate variability (HRV) and other beat-by-beat metric information. According to an example embodiment, the electronic system keeps the phase information of the signal and is able to identify when a specific heartbeat happens, in a time that can be related to absolute time. According to an example embodiment, the electronic system can process the audio signal and provide heartbeat information in real time, while the subject is generating the audio signal. According to an example embodiment, the electronic system provides for a synchronous demodulation of the audio signal based on the fundamental frequency of a vowel audio sound. According to an example embodiment, the system is able to automatically adapt to different subjects' voices, thus avoiding the need for training configuration phases.

According to an example embodiment, there is provided an electronic system for calculating cardiovascular heartbeat information from an electronic audio signal, wherein the electronic audio signal comprises information representative of a human voice signal in the time domain, the human voice signal comprising a vowel audio sound of a certain duration and a fundamental frequency; and wherein the electronic system comprises: a signal receiving module configured for receiving the electronic audio signal; an audio processing module configured for generating a power spectral profile of a section of the electronic audio signal, and for detecting the fundamental frequency in the generated power spectral profile; a denoising module configured for filtering the received audio signal within a band around at least the detected fundamental frequency and thereby generating a denoised audio signal; a signal transformation module configured for generating a time domain intermediate signal that captures frequency, amplitude and/or phase of the denoised audio signal; and a beat detection module configured for detecting and calculating heartbeat information within a human cardiac band in the intermediate signal.

According to an example embodiment, the signal transformation module is configured for receiving the denoised audio signal and calculating the Hilbert transform; the complex autocorrelation with M samples delay; and the instantaneous frequency, thereby generating a time domain intermediate signal capturing the frequency of the denoised audio signal.

According to an example embodiment, the signal transformation module is configured for generating an in-phase and quadrature signal of the denoised audio signal, with a carrier having a frequency that is the fundamental frequency; and calculating the $L^2$ norm of the in-phase and quadrature signals, thereby generating a time domain intermediate signal capturing the amplitude of the denoised audio signal.

According to an example embodiment, the signal transformation module is configured for generating an in-phase and quadrature signal of the denoised audio signal, with a carrier having a frequency that is the fundamental frequency; and calculating the phase of the in-phase and quadrature signals, thereby generating a time domain intermediate signal capturing the phase of the denoised audio signal.

According to an example embodiment, the denoising module is further configured for filtering the received audio signal also within bands around one or more multiples of the detected fundamental frequency and for generating one or more denoised audio signals.

According to an example embodiment, the denoising module is configured for generating a plurality of denoised audio signals and the signal transformation module is configured for combining calculation results from each of the denoised audio signals.

According to an example embodiment, the system further comprises a heart rate information calculation module configured for calculating HR and/or HRV information based on the heartbeat information provided by the beat detection module.

An example embodiment relates to an electronic device comprising the electronic system for calculating cardiovascular heartbeat information according to embodiments herein described.

An example embodiment relates to a method for, in an electronic system or device, calculating cardiovascular heartbeat information from an electronic audio signal, wherein the electronic audio signal comprises information representative of a human voice signal in the time domain, the human voice signal comprising a vowel audio sound of a certain duration and a fundamental frequency; and the method comprising: receiving the electronic audio signal; generating a power spectral profile of a section of the electronic audio signal, and detecting the fundamental frequency in the generated power spectral profile; filtering the received audio signal within a band around at least the detected fundamental frequency and thereby generating a denoised audio signal; generating a time domain intermediate signal that captures frequency, amplitude and/or phase of the denoised audio signal; and detecting and calculating heartbeat information within a human cardiac band in the intermediate signal.

According to an example embodiment, the step of generating a time domain intermediate signal that captures frequency of the denoised audio signal comprises: calculating a Hilbert transform; calculating a complex autocorrelation with M samples delay; and calculating the instantaneous frequency.

According to an example embodiment, the step of generating a time domain intermediate signal that captures amplitude of the denoised audio signal, comprises: generating an in-phase and a quadrature signal of the of the denoised audio signal, with a carrier having a frequency that is the fundamental frequency; and calculating the $L^2$ norm of the in-phase and quadrature signals.

According to an example embodiment, the step of generating a time domain intermediate signal that captures phase of the denoised audio signal (545), comprises: generating an in-phase and a quadrature signal of the of the denoised audio signal, with a carrier having a frequency that is the fundamental frequency; and calculating the phase of the in-phase and quadrature signals.

An example embodiment relates to a computer program product comprising computer program code means adapted for calculating cardiovascular heartbeat information according to the methods herein described when the program is run on a computer, and to a computer readable storage medium comprising such computer program.

BRIEF DESCRIPTION OF THE FIGURES

The above, as well as additional, features will be better understood through the following illustrative and non-limiting detailed description of example embodiments, with reference to the appended drawings.

All the figures are schematic, not necessarily to scale, and generally only show parts which are necessary to elucidate example embodiments, wherein other parts may be omitted or merely suggested.

DETAILED DESCRIPTION

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example. Furthermore, like numbers refer to the same or similar elements or components throughout.

In the following, in the description of example embodiments, various features may be grouped together in a single embodiment, figure, or description thereof for the purpose of streamlining the disclosure and aiding in the understanding of one or more of the various described aspects. This is however not to be interpreted as some embodiments requiring more features than the ones expressly recited in the main claim. Furthermore, combinations of features of different embodiments are meant to be within the scope of the disclosure, as would be clearly understood by those skilled in the art. Additionally, in other instances, well-known methods, structures and techniques have not been shown in detail in order not to obscure the conciseness of the description.

Figure 1:
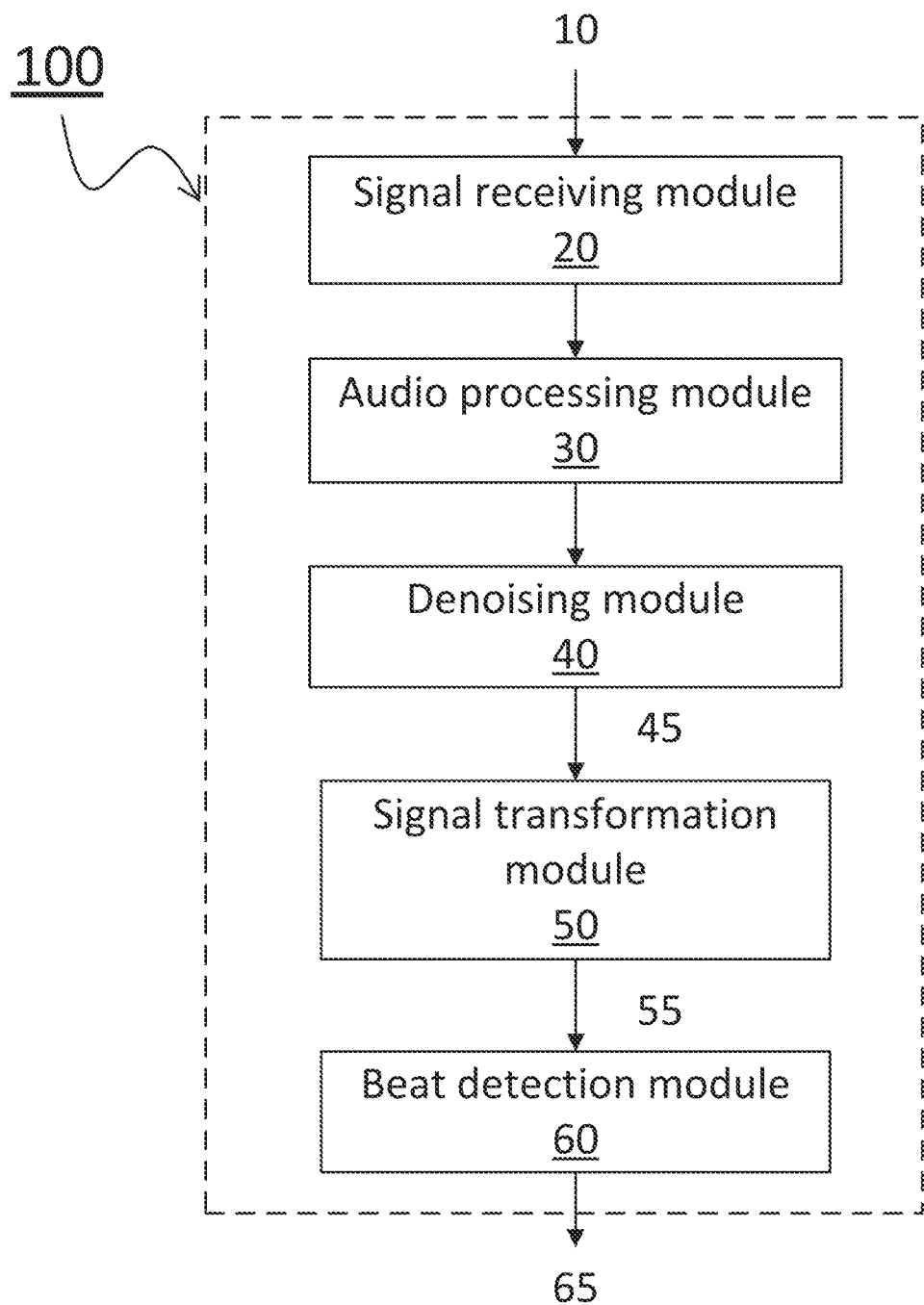
FIG. 1 shows a first general block diagram of an example system for calculating cardiovascular heartbeat information according to an example embodiment.

FIG. 1 shows a first general block diagram of an example system 100 for calculating cardiovascular heartbeat information from an electronic audio signal 10. The system comprises a signal receiving module 20, an audio processing module 30, a denoising module 40, a signal transformation module 50, and a beat detection module 60.

The electronic audio signal 10 comprises information representative of a subject's voice signal in the time domain.

Figure 4:
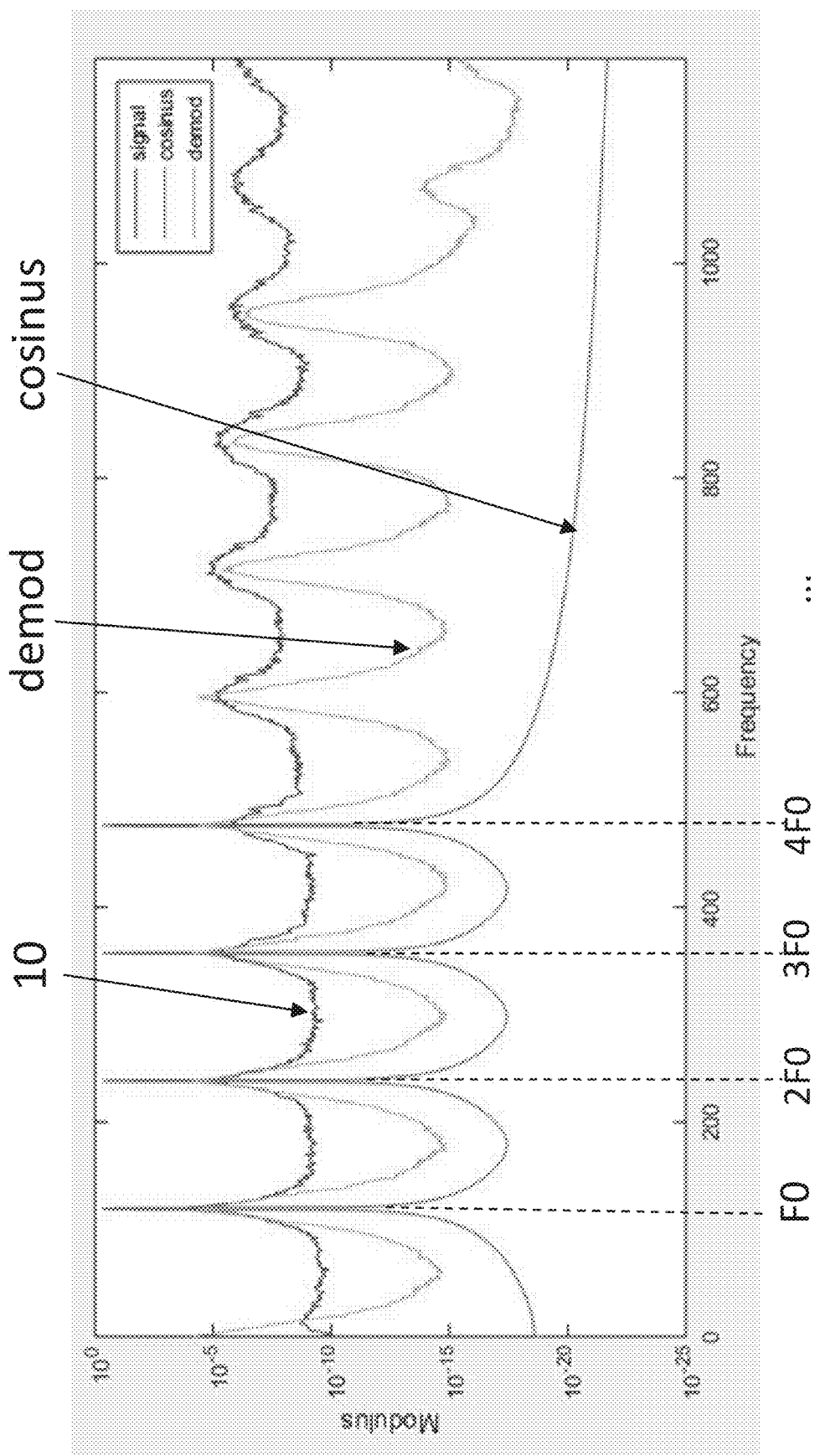
FIG. 4 illustrates a graph of an example electronic audio signal comprising a vowel audio sound having a fundamental frequency, in relation to other signals generated by the electronic system based on that fundamental frequency according to an example embodiment.

The subject's voice signal comprises a vowel audio sound of a certain duration and a fundamental frequency (F0 in FIG. 4). In some embodiments, the electronic audio signal 10 may comprise a vowel audio sound that the subject has to sustain for a certain period or a vowel sound that is extracted from the subject's speech (e.g. by recognizing a vowel sound that has a certain duration or by stitching a plurality of vowel sounds). According to example embodiments, the electronic audio signal 10 may comprise a vowel audio sound having a certain minimum duration so as to comprise a detectable fundamental frequency characteristic of that subject. The electronic audio signal 10 may be a real-time signal or may be a non-real time recorded signal that can be also postprocessed with a latency or in non-real time.

The signal receiving module 20 is configured for receiving the electronic audio signal 10, e.g. from an audio sensor or transducer, such as for example a microphone. In some embodiments, the signal receiving module 20 may comprise wired or wireless transmission/receiving means to receive such electronic audio signal. In some embodiments, the signal receiving module 20 may comprise a storage or memory in which such electronic audio signal is temporarily or permanently stored. In some embodiments, the signal receiving module 20 may just comprise means to read the electronic audio signal from a memory or storage unit. In embodiments, the electronic audio signal is an analogue or digital audio signal in the kHz range. In some embodiments, the signal receiving module 20 may comprise analogue to digital conversion and audio signal conditioning means.

The audio processing module 30 is configured for generating a power spectral profile of a section of the electronic audio signal 10 and detecting the fundamental frequency (F0 in FIG. 4) of the generated power spectral profile. According to an example embodiment, a small portion of the voice is extracted from the electronic audio signal 10, and from it a power spectral profile is computed (see FIG. 4). According to example embodiments, from the power spectral profile, around the first peak detected is considered the fundamental frequency of the voice signal. According to example embodiments, the audio processing module 30 may be also configured for calculating or detecting subsequent harmonics of the fundamental frequency, located at around 2, 3, 4, . . . N times the fundamental frequency.

The denoising module 40 is configured for filtering the received audio signal within a band around at least the detected fundamental frequency and thereby generating a denoised audio signal 45. According to example embodiments, the denoising unit performs a bandpass filtering of the electronic audio signal 10 around the fundamental frequency F0 to reduce the sources of noise and avoid aliasing. According to example embodiments, the bandpass filtering can be done up to about +/−10 Hz around the fundamental frequency. According to example embodiments, the denoising module may be further configured for filtering the received electronic audio signal 10 also within bands around one or more harmonics or multiples of the detected fundamental frequency (2F0, 3F0, . . . NF0 in FIG. 4) and for generating one or more denoised audio signals. According to example embodiments, the bandpass filtering can be also done up to about +/−10 Hz around the harmonics. For example, according to example embodiments, the denoising module 40 may generate a first denoised audio signal for the fundamental frequency and a second denoised audio signal for one of the corresponding harmonics. The denoising module 40 may generate also denoised audio signals for each of the harmonics (e.g. bandpass filtering the electronic audio signal 10 around the harmonic NF0). According to example embodiments, the denoising module may generate one denoised audio signal by bandpass filtering of the electronic audio signal 10 around the fundamental frequency F0 and around one or more harmonics.

The signal transformation module 50 is configured for generating a time domain intermediate signal 55 that captures frequency, amplitude and/or phase of the generated denoised audio signal 45. According to example embodiments, the signal transformation module may be configured for calculating the Hilbert transform of the denoised audio signal, the complex autocorrelation with M samples delay, and the instantaneous frequency, thereby generating a time domain intermediate signal capturing the frequency of the denoised audio signal. According to example embodiments, the signal transformation module may be configured for generating an in-phase and quadrature signal of the denoised audio signal, with a carrier having a frequency that is the fundamental frequency, and calculating the $L^2$ norm of the in-phase and quadrature signals over time, thereby generating a time domain intermediate signal capturing the amplitude of the denoised audio signal. According to example embodiments, the signal transformation module may be configured for generating an in-phase and quadrature signal of the denoised audio signal, with a carrier having a frequency that is the fundamental frequency; and calculating the phase of the in-phase and quadrature signals, thereby generating a time domain intermediate signal capturing the phase of the denoised audio signal. According to example embodiments, when the denoising module 40 is configured for generating a plurality of denoised audio signal 45 corresponding to the detected fundamental frequency and one or more harmonics, the signal transformation module is configured for combining calculated results from each of the denoised audio signals.

The beat detection module 60 is configured for detecting and calculating heartbeat information 65 within a human cardiac band in the intermediate signal 55. According to example embodiments, the human cardiac band is around 40 to 200 bpm or 0.5 Hz to 5.5 Hz. According to example embodiments, the beat detection module is configured to detect heartbeat information within a human cardiac band in the intermediate signal, on the time domain, the frequency domain and/or using wavelets techniques. According to example embodiments, the heartbeat information 65 comprises average heart rate, heartbeats and/or instantaneous heart rate. According to example embodiments, the beat detection module may be configured for performing a bandpass filtering of the intermediate signal around a human cardiac band.

Figure 2A:
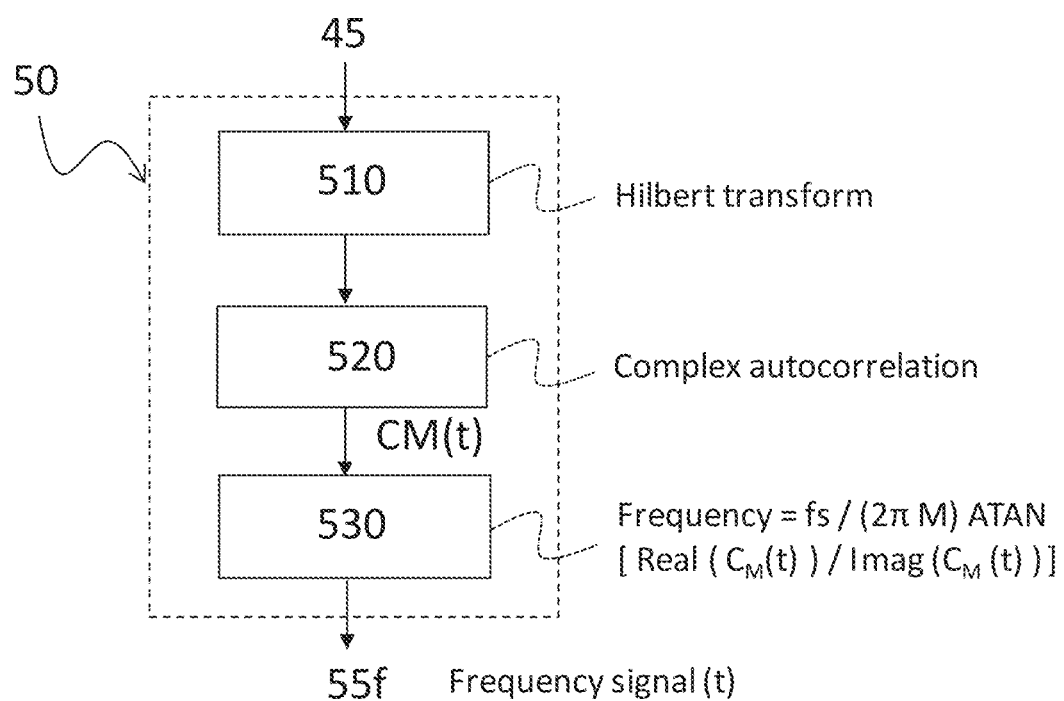
FIG. 2A shows a block diagram of a first example signal transformation module according to an example embodiment.

FIG. 2A shows a block diagram of a first example signal transformation module 50 configured for generating a time domain intermediate signal 55$f$ that captures the frequency of the generated denoised audio signal 45. According to example embodiments, the signal transformation module is configured for calculating the Hilbert transform of the received denoised audio signal, calculating the complex autocorrelation of the Hilbert transform with M samples delay $C_M(t)$, calculating the instantaneous frequency and low pass filtering the instantaneous frequency signal to avoid aliasing. According to example embodiments, the signal transformation module 50 may further be configured for down sampling the instantaneous frequency signal, which may be utilized for real-time operation processing. According to example embodiments, the down-sampling is done to a human cardiac-like sampling frequency, e.g. 256 Hz.

Figure 2B:
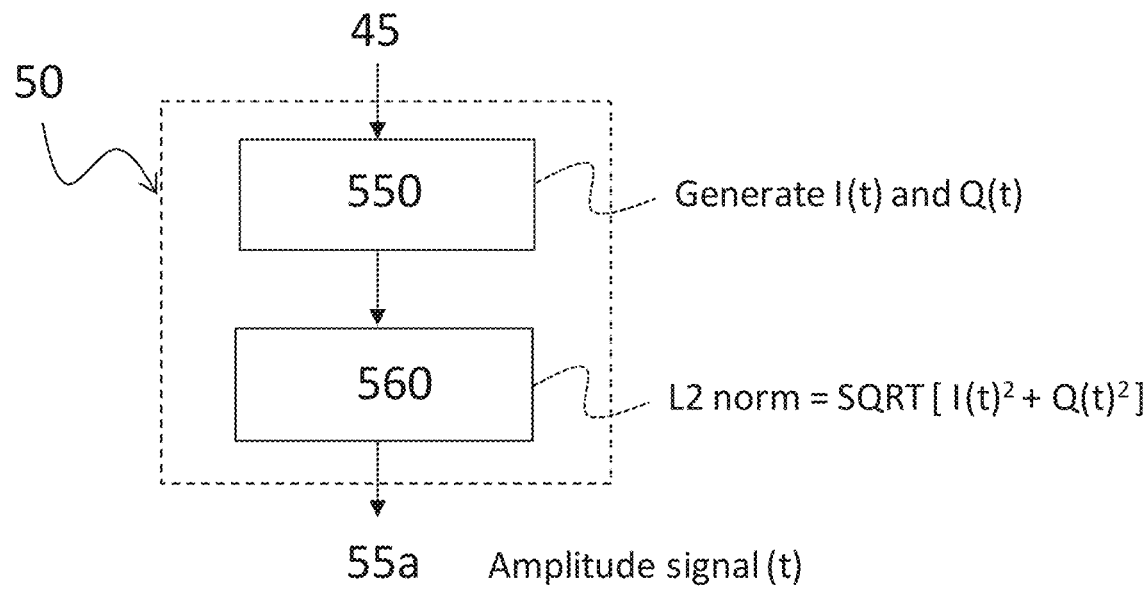
FIG. 2B shows a block diagram of a second example signal transformation module according to an example embodiment.

FIG. 2B shows a block diagram of a second example signal transformation module 50 configured for generating a time domain intermediate signal 55a that captures the amplitude of the generated denoised audio signal 45. According to example embodiments, the signal transformation module is configured for generating an in-phase I(t) and quadrature Q(t) signal of the denoised audio signal, with a carrier having a frequency that is the fundamental frequency and calculating the $L^2$ norm of the in-phase and quadrature signals. According to example embodiments, the signal transformation module is configured for: generating a sine wave having the fundamental frequency, and multiplying the denoised audio signal by the sine wave, thereby generating the in-phase signal I(t); generating a cosine wave having the fundamental frequency, and multiplying the denoised audio signal by the cosine wave, thereby generating the quadrature signal Q(t); and calculating the sample-by-sample square root of the sum of the squares of the in-phase and quadrature signals over time. According to example embodiments, the signal transformation module 50 may further be configured for low pass filtering and/or down sampling the in-phase I(t) and/or the quadrature signal Q(t), which may be useful for avoiding aliasing or for real-time operation processing. According to example embodiments, the down-sampling is done to a human cardiac-like sampling frequency, e.g. 256 Hz.

Figure 2C:
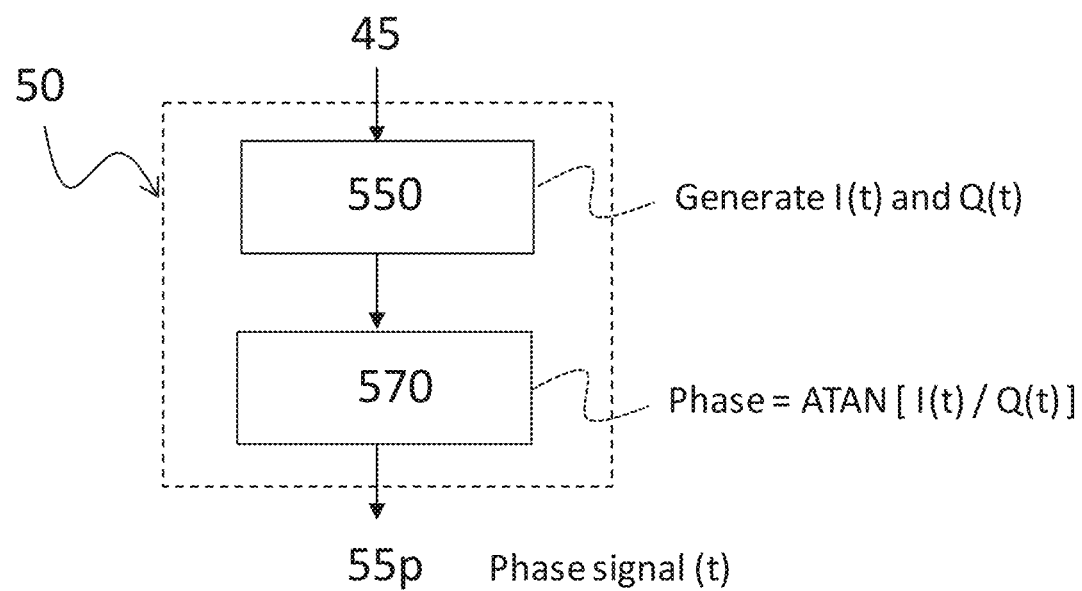
FIG. 2C shows a block diagram of a third example signal transformation module according to an example embodiment.

FIG. 2C shows a block diagram of a third example signal transformation module 50 configured for generating a time domain intermediate signal 55p that captures the amplitude of the generated denoised audio signal 45. According to example embodiments, the signal transformation module is configured for generating an in-phase I(t) and quadrature Q(t) signal of the denoised audio signal, with a carrier having a frequency that is the fundamental frequency and calculating the phase of the in-phase and quadrature signals. According to example embodiments, the signal transformation module is configured for: generating a sine wave having the fundamental frequency, and multiplying the denoised audio signal by the sine wave, thereby generating the in-phase signal I(t); generating a cosine wave having the fundamental frequency, and multiplying the denoised audio signal by the cosine wave, thereby generating the quadrature signal Q(t); and calculating the arctangent of the in-phase signal divided by the quadrature signal. According to example embodiments, the signal transformation module may be configured for compensating the phase by 2 pi shifts in order to enforce signal continuity. According to example embodiments, the signal transformation module 50 may further be configured for low pass filtering and/or down sampling the in-phase I(t) and/or the quadrature signal Q(t), which may be useful for avoiding aliasing or for real-time operation processing. According to example embodiments, the down-sampling is done to a human cardiac-like sampling frequency, e.g. 256 Hz.

Figure 3:
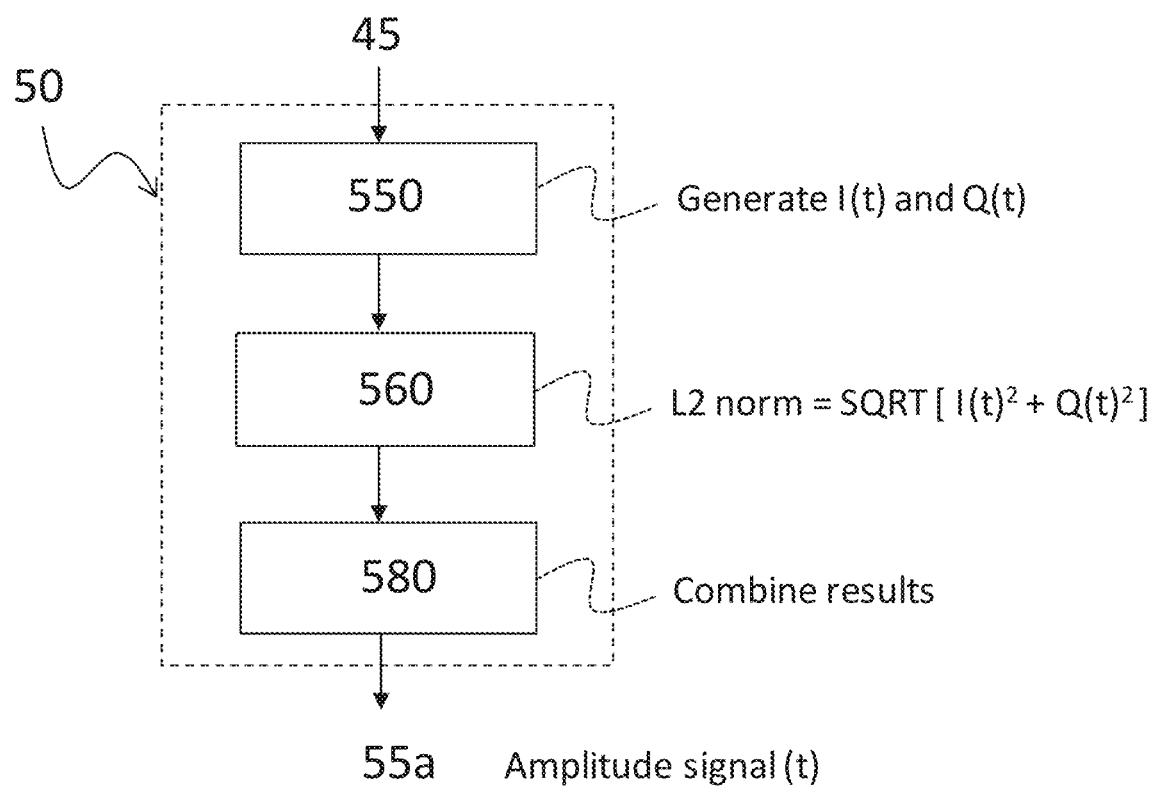
FIG. 3 shows a block diagram of a fourth example signal transformation module according to an example embodiment.

FIG. 3 shows a block diagram of a fourth example signal transformation module 50 configured for generating a time domain intermediate signal 55a that captures the amplitude of a plurality of generated denoised audio signal 45. According to example embodiments, the signal transformation module is configured for: generating an in-phase I(t) and quadrature Q(t) signal for each of a plurality of denoised audio signals (e.g. one corresponding to the fundamental frequency and at least another one corresponding to one harmonic), with a carrier having a frequency that is the fundamental frequency; calculating the modulus of the in-phase and quadrature signals; and combining calculated amplitude results from each of the denoised audio signals.

According to example embodiments, the signal transformation module is configured for: generating an in-phase I(t) and quadrature Q(t) signal for each of a plurality of denoised audio signals (e.g. one corresponding to the fundamental frequency and at least another one corresponding to one harmonic), with a carrier having a frequency that is the fundamental frequency; combining generated in-phase I(t) and quadrature Q(t) signal values for each of the denoised audio signals; and calculating the modulus of the combined in-phase and quadrature signals.

Although FIG. 3 only shows an example for a signal transformation module 50 configured for generating a time domain intermediate signal 55a that captures the amplitude of a plurality of generated denoised audio signals 45, similar combinations can be done for a signal transformation module 50 configured for generating a time domain intermediate signal 55p that captures the phase of a plurality of generated denoised audio signals 45. According to example embodiments, the signal transformation module is configured for: combining the received denoised audio signals; calculating the Hilbert transform of the combined audio signals; calculating the complex autocorrelation with M samples delay $C_M(t)$; calculating the instantaneous frequency, and low pass filtering the instantaneous frequency signal. According to example embodiments, the signal transformation module is configured for: calculating the Hilbert transform of each of the received denoised audio signals; calculating the complex autocorrelation with M samples delay $C_M(t)$ of each of the received denoised audio signals; calculating the instantaneous frequency for each of the $C_M(t)$; combining the instantaneous frequencies and low pass filtering the instantaneous frequency signal.

FIG. 4 illustrates a graph of an example electronic audio signal 10 in frequency domain, comprising a vowel audio sound having a fundamental frequency F0, and a plurality of harmonics 2F0, 3F0, 4F0, . . . NF0. Further example demodulation signals generated by the signal transformation module 50 are also shown together with the synthetically generated cosine signal with frequencies F0 and a plurality of harmonics 2F0, 3F0, 4F0 used in the demodulation process. It shall be noted that the frequency content of the input signal at the DC level is low to non-existing, whereas the demodulated signal levels in the DC area reflects the contents of the bands around the harmonics in the input signal. Such bandwidth contains the cardiac information to be decoded.

Figure 5:
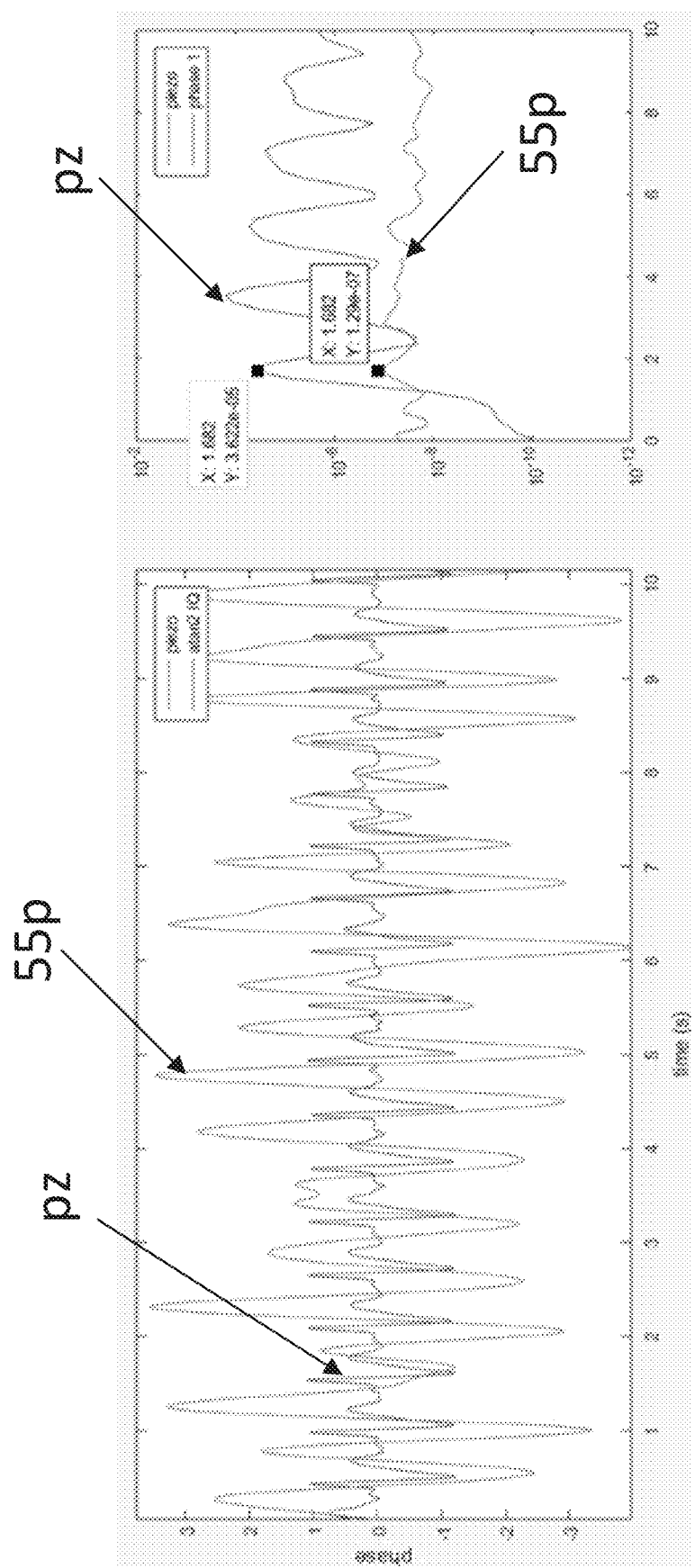
FIG. 5 illustrates a graph of an example time domain intermediate signal with phase information, generated by the signal transformation module, and the comparison of the intermediate signal and a primary cardiac pulse signal in the frequency domain, showing the same location of the first harmonic according to an example embodiment.

FIG. 5 illustrates a graph, in time domain (left) and frequency domain (right), of an example intermediate signal 55p with phase information, generated by the signal transformation module 50. The intermediate signal 55p is compared with a reference cardiac pulse signal pz from a piezo-based sensor in the thumb measuring volumetric displacement. The time domain graph (left) shows how the pulsatility of the signal 55p is similar to that of the reference cardiac pulse piezo signal pz. The frequency domain signal (right) reflects that the fundamental frequency of both the signals 55p (highest frequency peak) and reference pz (first peak) are in the exact same frequency location.

Figure 6:
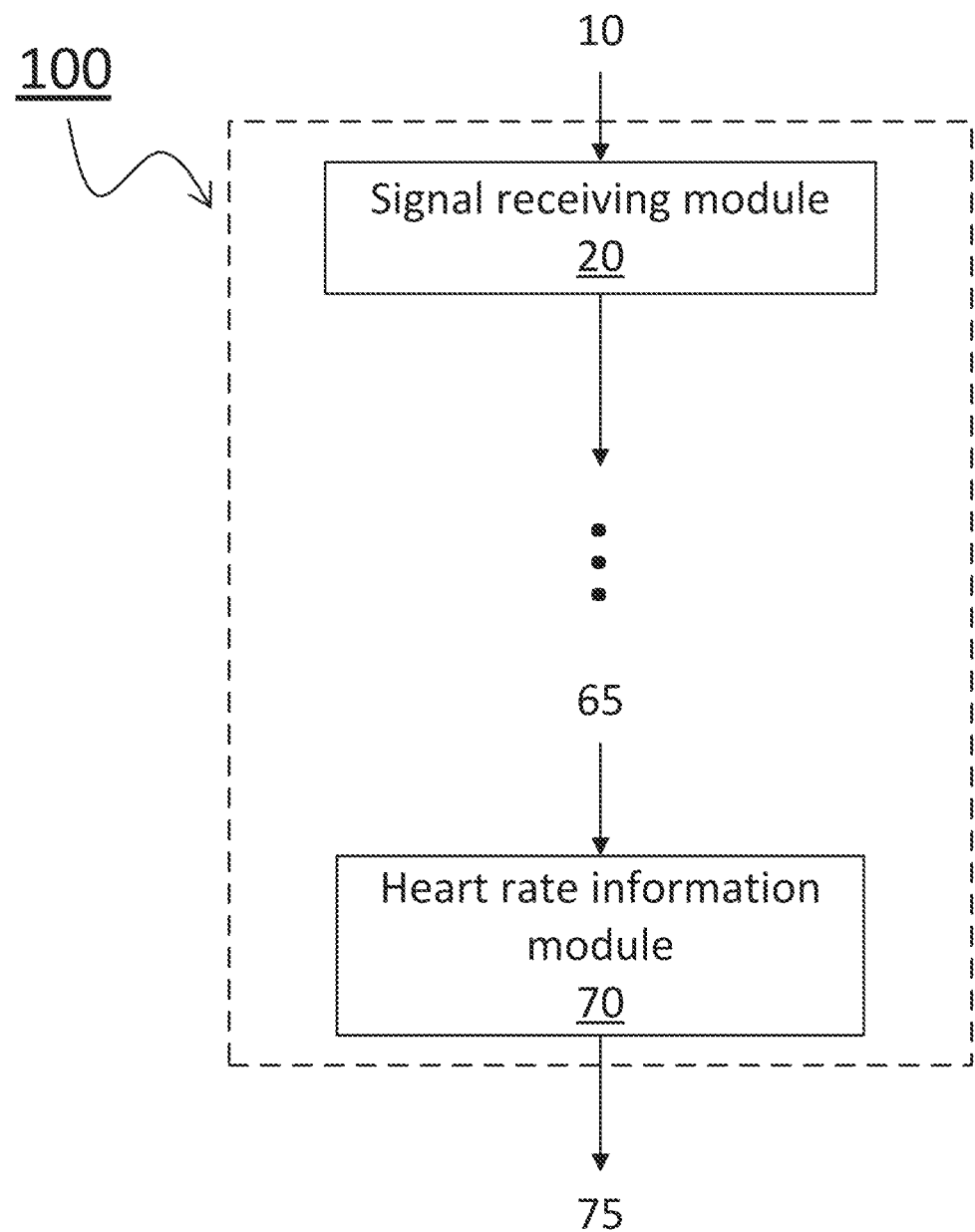
FIG. 6 shows a second general block diagram of an example system for calculating cardiovascular heartbeat information, further comprising a heart rate information calculation module providing HR and/or HRV information according to an example embodiment.

FIG. 6 shows a second general block diagram of an example system 100 for calculating cardiovascular heartbeat information from an electronic audio signal 10, further comprising a heart rate information module 70. The heart rate information module is configured to receive heartbeat information 65 from the beat detection module 60 and calculate beat-to-beat information 75 such as beat-to-beat time delay, HRV and/or heart rate. According to example embodiments, the signal transformation beat detection module 60 and/or the heart rate information module 70 may provide information based on any of the time domain intermediate signals 55 generated by the signal transformation module 50. According to example embodiments, the signal transformation beat detection module 60 and/or the heart rate information module 70 may provide multiple information based on a plurality of time domain intermediate signals 55f, 55a, 55p generated by the signal transformation module 50. According to example embodiments, the signal transformation beat detection module 60 and/or the heart rate information module 70 may provide information based on a weighted or quality-related values derived from a plurality of time domain intermediate signals 55f, 55a, and 55p.

It shall be noted that the system 100 for calculating cardiovascular heartbeat information according to embodiments of the disclosure may be implemented according to hardware and/or software state of the art techniques, comprising for example a microprocessor, microcontroller or digital signal processor that can understand and execute software program instructions. Some programmable hardware logic, application-specific integrated circuit (ASIC), and/or memory means may be specifically designed also for executing the method or parts of it according to example embodiments of the disclosure. The system may be implemented in an electronic device. The electronic device may be a wearable or a tethered device. The system may work in real time, almost real time (with a latency) or in post-processing.

Figure 7:
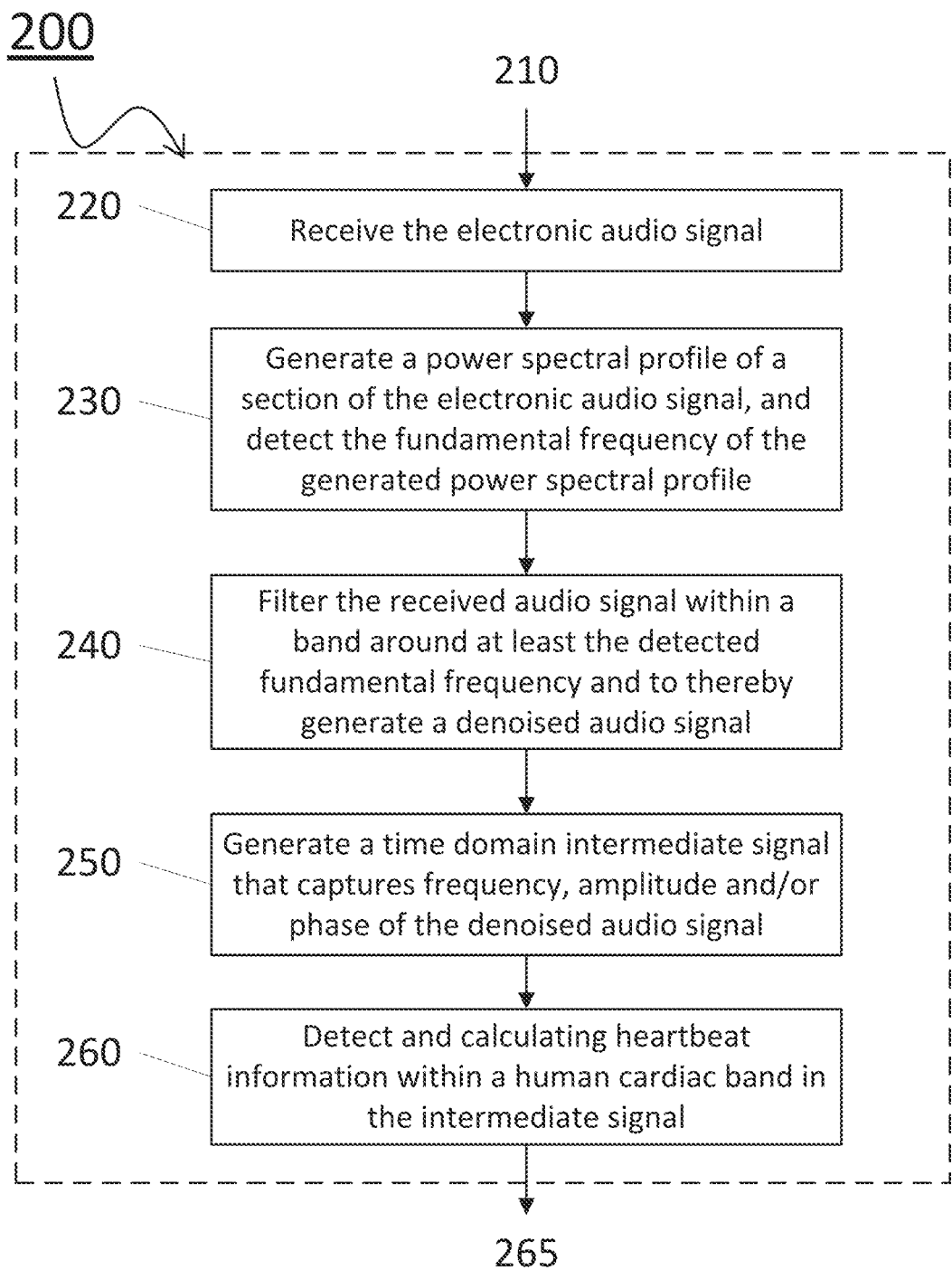
FIG. 7 shows an example flow diagram for calculating cardiovascular heartbeat information from an electronic audio signal according to an example embodiment.

FIG. 7 shows an example flow diagram 200 for calculating cardiovascular heartbeat information from an electronic audio signal 210. The method may be implemented in an electronic system or device, such as the ones described herein, or in a computer or processing unit. The electronic audio signal comprises information representative of a human voice signal in the time domain, the human voice signal comprises a vowel audio sound of a certain duration and a fundamental frequency. The method comprises: 220, receiving the electronic audio signal; 230, generating a power spectral profile of a section of the electronic audio signal, and detecting the fundamental frequency of the generated power spectral profile; 240, filtering the received audio signal within a band around at least the detected fundamental frequency and thereby generating a denoised audio signal 245; 250, generating a time domain intermediate signal 255 that captures frequency, amplitude and/or phase of the denoised audio signal; and 260, detecting and calculating heartbeat information 265 within a human cardiac band in the intermediate signal.

According to example embodiments, the human cardiac band is around 40 to 200 bpm or 0.6 Hz to 3.5 Hz. According to example embodiments, the step 260 of detecting and calculating heartbeat information 265 within a human cardiac band in the intermediate signal, can be performed, for example, on the time domain, the frequency domain and/or using wavelets techniques. According to example embodiments, the heartbeat information 265 comprises average heart rate, heartbeats and/or instantaneous heart rate. According to example embodiments, the step 260 of detecting and calculating heartbeat information may comprise bandpass filtering of the intermediate signal 255 around a human cardiac band.

Figure 8A:
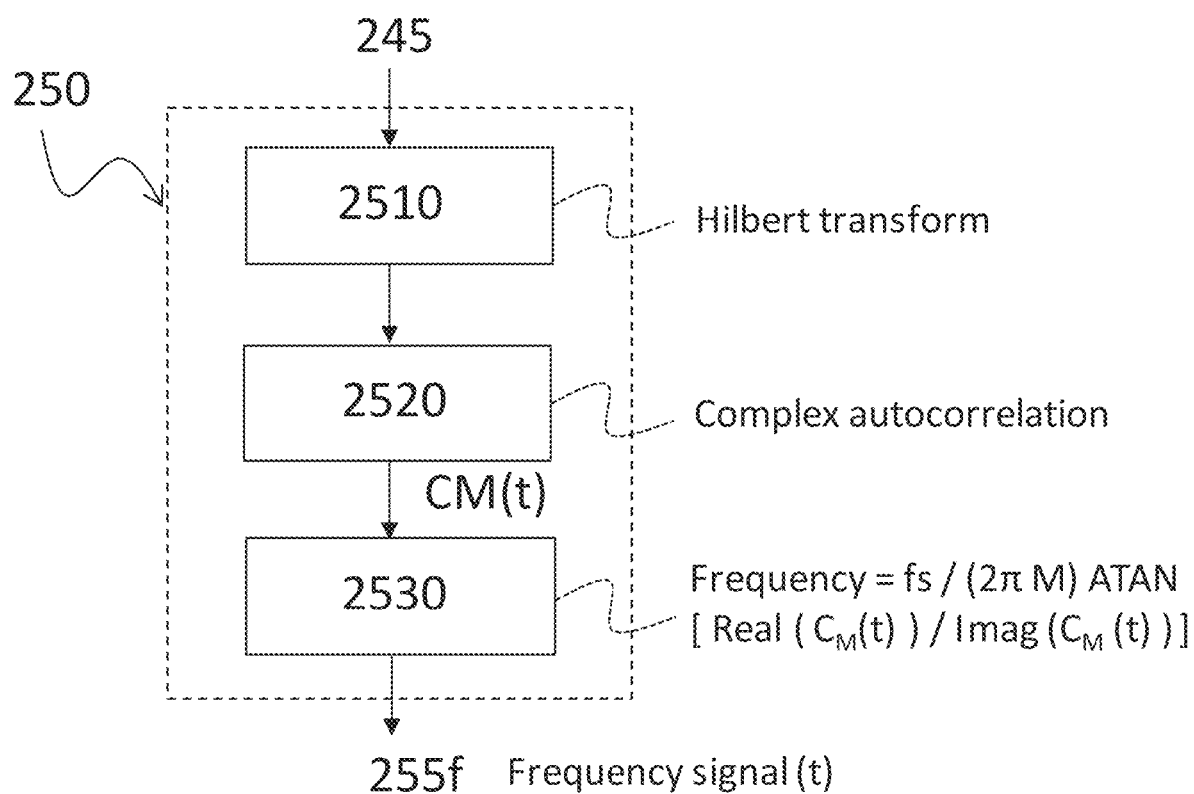
FIG. 8A shows a first example flow diagram for generating a time domain intermediate signal that captures frequency information according to an example embodiment.

FIG. 8A shows a first example flow diagram for the step 250 of generating a time domain intermediate signal 255f that captures frequency information. The method comprises: 2510, calculating a Hilbert transform of the denoised audio signal 245; 2520, calculating a complex autocorrelation with M samples delay of the Hilbert transform; and 2530, calculating the instantaneous frequency.

Figure 8B:
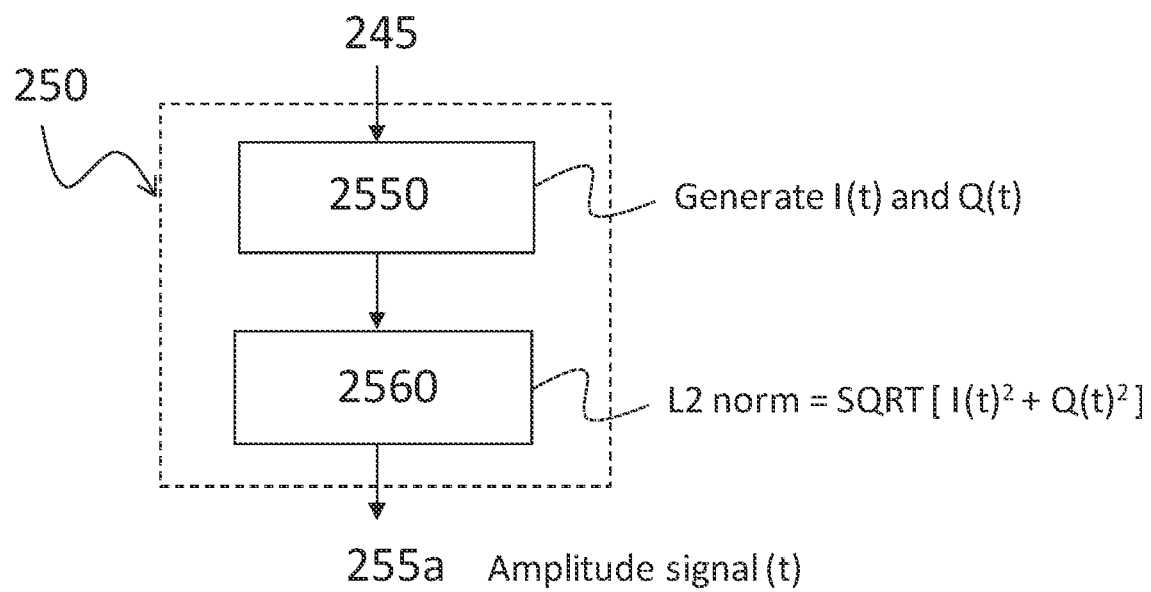
FIG. 8B shows a second example flow diagram for generating a time domain intermediate signal that captures amplitude information according to an example embodiment.

FIG. 8B shows a second example flow diagram for the step 250 of generating a time domain intermediate signal 255a that captures amplitude information. The method comprises: 2550, generating an in-phase and a quadrature signal of the denoised audio signal 245, with a carrier having a frequency that is the fundamental frequency; and 2560, calculating the $L^2$ norm of the in-phase and quadrature signals.

Figure 8C:
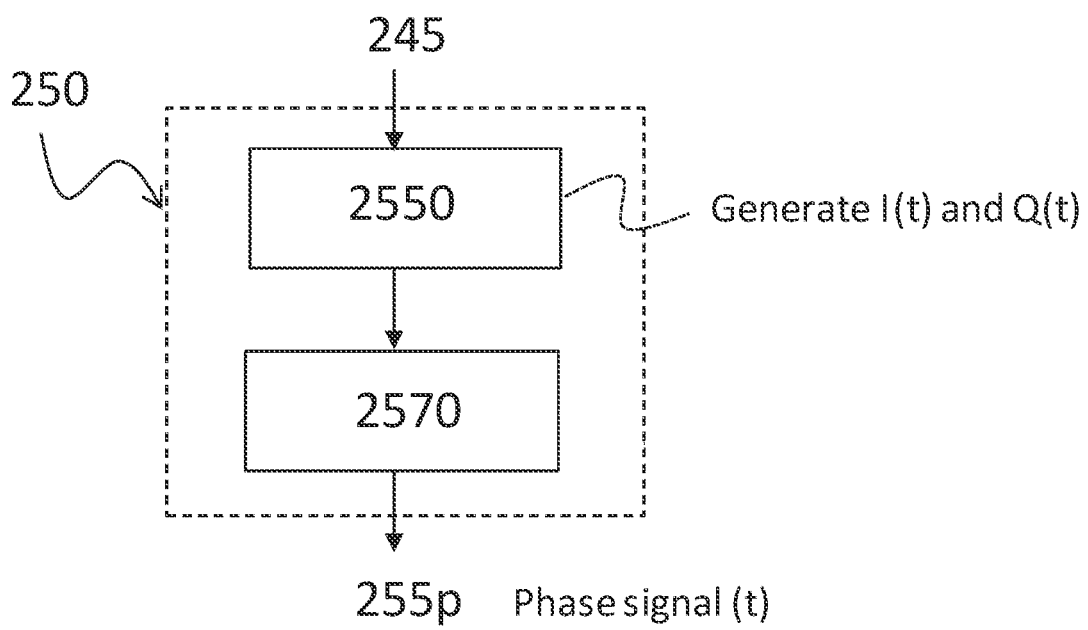
FIG. 8C shows a third example flow diagram for generating a time domain intermediate signal that captures phase information according to an example embodiment.

FIG. 8C shows a third example flow diagram for the step 250 of generating a time domain intermediate signal 255p that captures phase information. The method comprises: 2550, generating an in-phase and a quadrature signal of the denoised audio signal, with a carrier having a frequency that is the fundamental frequency; and 2570, calculating the phase of the in-phase and quadrature signals.

Figure 9:
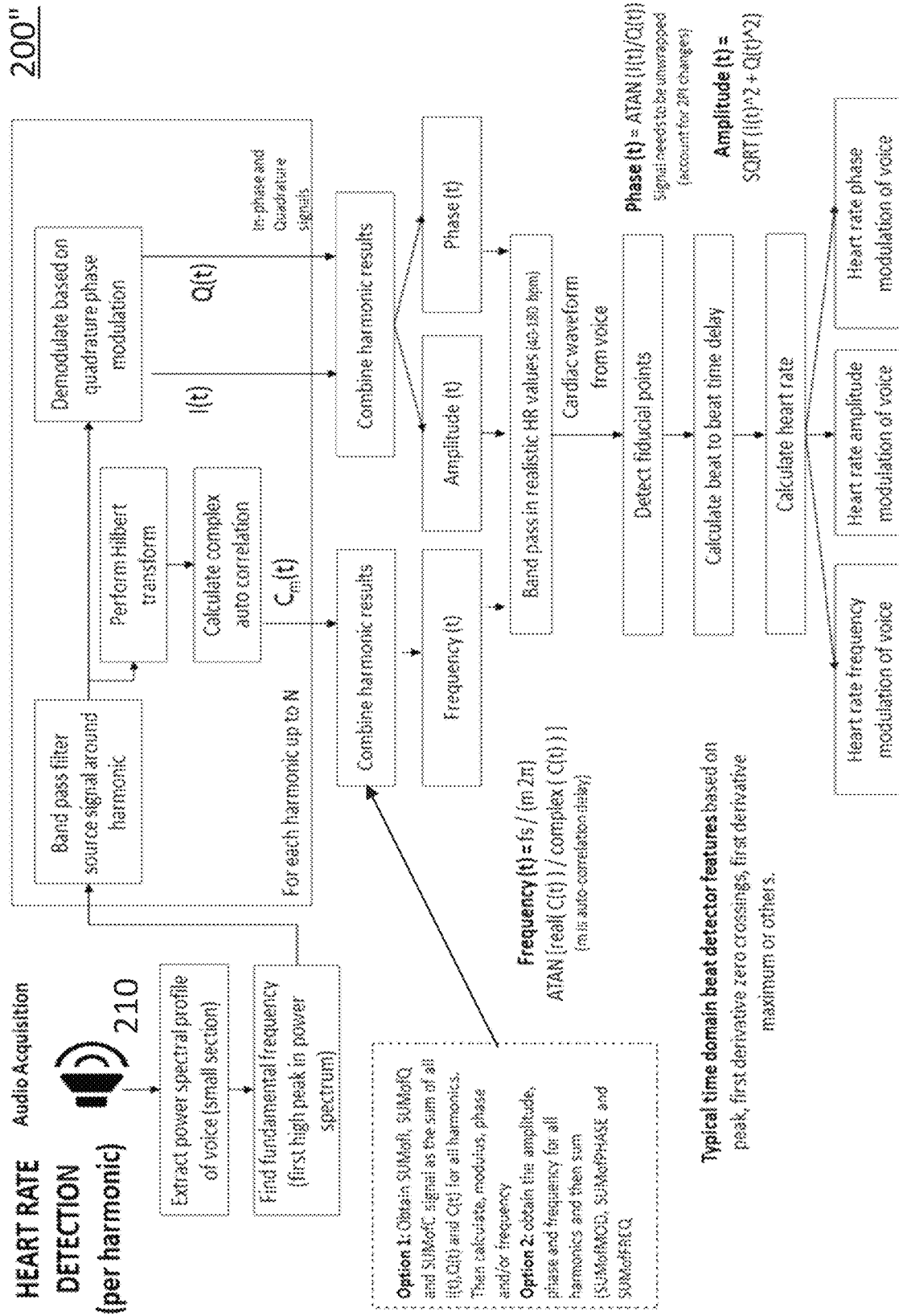
FIG. 9 shows a second example flow diagram for calculating cardiovascular heartbeat information from an electronic audio signal according to an example embodiment.

FIG. 9 shows a second example flow diagram 200' for calculating cardiovascular heartbeat information from an electronic audio signal 210. According to an example embodiment, the electronic audio signal 210 may be generated by an audio acquisition module comprising a sensor (microphone), digitizer and signal conditioning of the audio signal. The output of the acquisition is a digital audio signal at a voice like sample rate (in the kHz range). According to embodiments, the electronic audio signal 210 may be just stored on a memory or storage unit and read. According to embodiments, the electronic audio signal 210 may be just received by wired or wireless transmission means. According to an example embodiment, the method comprises extracting a power spectral profile of a small section of the electronic audio signal. According to embodiments, a small portion of the voice is extracted and from it a power spectral profile is computed. According to an example embodiment, the method comprises detecting the fundamental frequency of the voice signal from the power spectral profile. According to an embodiment, the first peak of the power spectral profile is the fundamental frequency. Based on the detection of the fundamental frequency the subsequent harmonics should be at 2, 3, 4, etc. times the fundamental frequency. The method can be performed up to N harmonics. According to certain embodiments, the method is performed for N=4, as higher number of harmonics do not provide substantially better results but represent a higher computation expense. According to an example embodiment, for each of the harmonics until N, the method comprises:

1. Denoising the signal around the harmonic to reduce the sources of noise, e.g. typically +/−10 Hz around the Harmonic;
2a. Demodulating the signal following these steps
    Generating a Sine of the frequency of the Harmonic;
    Multiplying the filtered harmonic signal by the Sine, which results in the I(t) signal (In-phase);
    Optionally: low pass filtering the I(t) signal to avoid aliasing
    Optionally: down sampling the I(t) signal to a Cardiac-like (256 Hz for instance) sampling frequency.
    Generating a Cosine of the frequency of the Harmonic;
    Multiplying the filtered harmonic signal by the Cosine, which results in the Q(t) signal (Quadrature);
    Optionally: Low pass filtering the Q(t) signal to avoid aliasing;
    Optionally: Down sampling the Q(t) signal to a Cardiac-like (256 Hz for instance) sampling frequency.
2b. Performing complex autocorrelation, as alternative or in addition to demodulation method 2a, following these steps:
    Calculating the Hilbert transform of the signal;

Calculating the complex autocorrelation with m samples delay: $C_M(t)$;

Calculating the phase, $\phi(t)$, of the complex autocorrelation signal, i.e. the arctangent of the real divided by the complex part of $C_M(t)$;

Calculating the instantaneous frequency from the phase according to the following equation:

$$f = fs * \phi(t)/(2\pi m),$$

where fs is sampling frequency;

Low pass filtering the Cm(t) signal to avoid aliasing;

Optionally: Down sampling the Cm(t) signal to a cardiac-like (256 Hz for instance) sampling frequency.

3. Combining Harmonic results. The results from the harmonics need to be combined to generate a consolidated amplitude and phase signals. Two of the possible options for combination are the following:

3.1 Option 1: summing all the results: get the sum of I(t) for all harmonics, and same for Q(t). Then compute the frequency, amplitude and phase. Amplitude is the square root of the sum of the squares of I(t) and Q(t). Phase is the arctangent of I(t)/Q(t), which may be compensated by 2 pi shifts. Instantaneous frequency: calculate the phase, $\phi(t)$, of the complex autocorrelation signal, i.e. the arctangent of the real divided by the complex part of Cm(t). The instantaneous frequency is calculated from phase, $\phi(t)$ according to the following equation:

$$f\text{inst} = fs * \phi(t)/(2\pi m),$$

where fs is sampling frequency.

3.2 Option 2: Calculating all amplitude and phase and sum: for each of the harmonics compute an amplitude and phase, sum the results.

Bandpass frequency, amplitude and phase signals: the extracted frequency, amplitude and phase modulations in the voice are filtered in the bandwidth of interest of Cardiac systems. This is roughly in the bandwidth corresponding to heart rates between 40 and 200 beats per minute. It is key that the filtering delay of the pulse needs to be controlled and accounted for, as it needs to be compensated.

According to an example embodiment, the method further comprises: optionally, performing a bandpass of the frequency, amplitude and phase signals: the extracted frequency, amplitude and phase modulations in the voice are filtered in the bandwidth of interest of Cardiac systems. This is roughly in the bandwidth corresponding to heart rates between 40 and 200 beats per minute. When bandpass filtering is applied, the filtering delay of the pulse needs to be controlled and accounted for, as it needs to be compensated. This delay may also be accounted for by design or compensated during a configuration phase.

According to an example embodiment, the method further comprises: extracting frequency, amplitude and phase relevant points from the signal related to heart beat information. This may be done in the time domain, frequency domain or using wavelets. According to an example embodiment, a time fiducial points are extracted from the amplitude and phase, which is characteristic of every beat in the signal. Such fiducial point can be based on peak detection in the signal or its derivatives, zero crossings or other time domain fiducial points. It should be characteristic for each of the beats.

According to an example embodiment, the method further comprises calculating heartbeat information, e.g. calculating beat to beat time delay. According to an example embodiment, once the signal points are detected for all the beats, the timing of point N is subtracted from the time in point N+1 to obtain the beat to beat time period.

According to an example embodiment, the method may further comprise calculating heart rate, e.g. the inverse is computed resulting in the heart rate. According to an example embodiment, three different heart rate signals may be obtained: heart rate extracted from the voice frequency signal over time; heart rate extracted from the voice amplitude signal over time; heart rate extracted from the voice phase signal over time.

Figure 10:
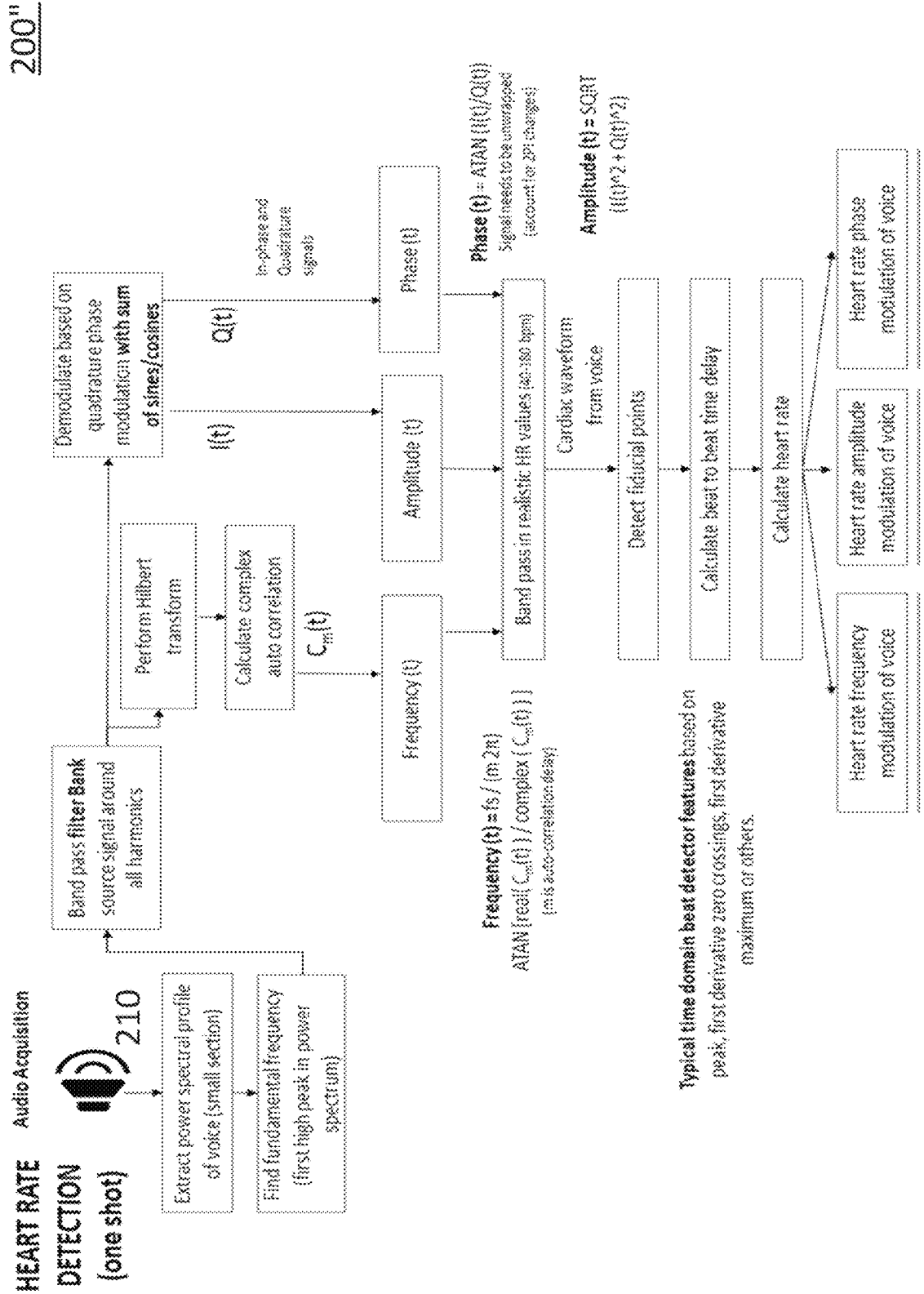
FIG. 10 shows a third example flow diagram for calculating cardiovascular heartbeat information from an electronic audio signal according to an example embodiment.

FIG. 10 shows a third example flow diagram 200″ for calculating cardiovascular heartbeat information from an electronic audio signal 210. According to an example embodiment, as an alternative to the block diagram per harmonic as shown in FIG. 9, the denoised audio signal can be also processed at once (not per harmonic as in FIG. 9). According to an example embodiment, the step of filtering the received audio signal within a band around at least the detected fundamental frequency and thereby generating a denoised audio signal 245, comprises performing multiple band pass filters preserving the bandwidth around all the selected N harmonics (e.g. typically +/−10 Hz around each of the harmonics). This may be a composite filtering resulting from linearly combining filters for all the harmonics. According to an example embodiment, for the demodulation option, demodulating the signal by Generating a signal including the sum of sines of the first N harmonics according to the following equation:

$$x(t) = \sin(2\text{pi } f1) + \sin(2\text{pi } f2) + \sin(2\text{pi } f3) +$$

Generating a signal including the sum of cosines of the first N harmonics according to the following equation:

$$y(t) = \cos(2\text{pi } f1) + \cos(2\text{pi } f2) + \cos(2\text{pi } f3) + \ldots.$$

Multiplying the filtered audio by x(t) to get I(t)

Multiplying the filtered audio by y(t) to get Q(t)

According to an example embodiment, for the complex autocorrelation: performing the Hilbert transform of the filtered signal containing all harmonics (instead of doing it per harmonic). The other processing steps are equal as described above for FIG. 9.

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings, the disclosure, and the appended claims. The mere fact that certain measures or features are recited in mutually different dependent claims does not indicate that a combination of these measures or features cannot be used. Any reference signs in the claims should not be construed as limiting the scope.

What is claimed is:

1. An electronic system for calculating cardiovascular heartbeat information from an electronic audio signal, wherein the electronic audio signal comprises information representative of a human voice signal in the time-domain, the human voice signal comprising a vowel audio sound of a certain duration and a fundamental frequency (F0); and wherein the electronic system comprises:

a signal receiving module configured to receive the electronic audio signal;

an audio processing module configured to generate a power spectral profile of a section of the electronic audio signal, and to detect the fundamental frequency (F0) in the generated power spectral profile;

a denoising module configured to filter the received audio signal within a band around at least the detected fundamental frequency (F0) to thereby generate a denoised audio signal;

a signal transformation module configured to generate a time-domain intermediate signal that captures one or more of: a frequency, an amplitude, or phase of the denoised audio signal; and a beat detection module configured to detect and calculate heartbeat information, within a human cardiac band, in the intermediate signal.

2. The system according to claim 1, wherein the signal transformation module is configured to receive the denoised audio signal and calculate a Hilbert transform; a complex autocorrelation M samples delay; and an instantaneous frequency, to thereby generating the time-domain intermediate signal that captures the frequency of the denoised audio signal.

3. The system according to claim 2, wherein the signal transformation module is configured to generate an in-phase (I) and quadrature (Q) signal of the denoised audio signal, with a carrier having a frequency that is the fundamental frequency (F0); and calculate an $L^2$ norm of the in-phase and quadrature signals, thereby generating the time domain intermediate signal capturing the amplitude of the denoised audio signal.

4. The system according to claim 2, wherein the signal transformation module (50) is configured to generate an in-phase (I) and quadrature (Q) signal of the denoised audio signal, with a carrier having the frequency that is the fundamental frequency (F0); and calculate the phase of the in-phase and quadrature signals, thereby generating the time domain intermediate signal capturing the phase of the denoised audio signal.

5. The system according to claim 2, wherein the denoising module is further configured to filter the received audio signal also within bands around one or more multiples of the detected fundamental frequency (F0) and to generate one or more denoised audio signals.

6. The system according to claim 1, wherein the signal transformation module is configured to generate an in-phase (I) and quadrature (Q) signal of the denoised audio signal, with a carrier having a frequency that is the fundamental frequency (F0); and calculate an $L^2$ norm of the in-phase and quadrature signals, thereby generating a time domain intermediate signal capturing the amplitude of the denoised audio signal.

7. The system according to claim 6, wherein the signal transformation module (50) is configured to generate the in-phase (I) and quadrature (Q) signal of the denoised audio signal, with the carrier having a frequency that is the fundamental frequency (F0); and calculate the phase of the in-phase and quadrature signals, thereby generating the time domain intermediate signal capturing the phase of the denoised audio signal.

8. The system according to claim 6, wherein the denoising module is further configured to filter the received audio signal also within bands around one or more multiples of the detected fundamental frequency (F0) and to generate one or more denoised audio signals.

9. The system according to claim 1, wherein the signal transformation module is configured to generate an in-phase (I) and quadrature (Q) signal of the denoised audio signal, with a carrier having a frequency that is the fundamental frequency (F0); and calculate the phase of the in-phase and quadrature signals, to thereby generate a time-domain intermediate signal that captures the phase of the denoised audio signal.

10. The system according to claim 9, wherein the denoising module is further configured to filter the received audio signal also within bands around one or more multiples of the detected fundamental frequency (F0) and to generate one or more denoised audio signals.

11. The system according to claim 1, wherein the denoising module is further configured to filter the received audio signal also within bands around one or more multiples of the detected fundamental frequency (F0) and to generate one or more denoised audio signals.

12. The system according to claim 11, wherein the denoising module is configured to generate a plurality of denoised audio signals and the signal transformation module is configured to combine calculation results from each of the denoised audio signals.

13. The system according to claim 1, further comprising a heart rate information calculation module configured to calculate heart rate (HR) and/or heart rate variability (HRV) information based on the heartbeat information.

14. An electronic device comprising the electronic system to calculate cardiovascular heartbeat information according to claim 1.

15. A method implemented by an electronic system or device for calculating cardiovascular heartbeat information from an electronic audio signal, wherein the electronic audio signal comprises information representative of a human voice signal in the time-domain, the human voice signal comprising a vowel audio sound of a certain duration and a fundamental frequency (F0); and the method comprising:

receiving the electronic audio signal;

generating a power spectral profile of a section of the electronic audio signal;

detecting the fundamental frequency (F0) in the generated power spectral profile;

filtering the received audio signal within a band around at least the detected fundamental frequency (F0) and thereby generating a denoised audio signal;

generating a time-domain intermediate signal that captures one or more of: a frequency, an amplitude, or phase of the denoised audio signal; and detecting and calculating heartbeat information within a human cardiac band in the intermediate signal.

16. The method according to claim 15, wherein generating the time-domain intermediate signal that captures the frequency of the denoised audio signal comprises: calculating a Hilbert transform; calculating a complex autocorrelation with M samples delay; and calculating an instantaneous frequency.

17. The method according to claim 16, wherein generating the time-domain intermediate signal that captures the amplitude of the denoised audio signal, comprises: generating an in-phase (I) and a quadrature signal (Q) of the denoised audio signal, with a carrier having a frequency that is the fundamental frequency (F0); and calculating a $L^2$ norm of the in-phase and quadrature signals.

18. The method according to claim 17, wherein generating the time domain intermediate signal that captures the phase of the denoised audio signal, comprises: generating an in-phase (I) and a quadrature (Q) signal of the of the denoised audio signal, with a carrier having the frequency that is the fundamental frequency (F0); and calculating the phase of the in-phase and quadrature signals.

19. A computer program product comprising computer program code that facilitates calculating cardiovascular heartbeat information according to the method of claim 15 when the program is run on a computer.

20. A non-transitory computer-readable storage medium comprising the computer program according to claim 19.

* * * * *